US011577084B2

(12) United States Patent
Andersen

(10) Patent No.: US 11,577,084 B2
(45) Date of Patent: Feb. 14, 2023

(54) METHOD AND DEVICE FOR MANAGING BIOLOGICAL ACTIVITY DATA STORAGE UTILIZING LOSSY COMPRESSION

(71) Applicant: Pacesetter, Inc., Sylmar, CA (US)

(72) Inventor: Dean P. Andersen, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 50 days.

(21) Appl. No.: 16/842,904

(22) Filed: Apr. 8, 2020

(65) Prior Publication Data

US 2021/0316151 A1 Oct. 14, 2021

(51) Int. Cl.
| | |
|---|---|
| *A61N 1/372* | (2006.01) |
| *A61N 1/02* | (2006.01) |
| *A61N 1/362* | (2006.01) |
| *A61N 1/08* | (2006.01) |
| *A61N 1/36* | (2006.01) |
| *A61N 1/05* | (2006.01) |

(52) U.S. Cl.
CPC ......... *A61N 1/37252* (2013.01); *A61N 1/025* (2013.01); *A61N 1/0563* (2013.01); *A61N 1/08* (2013.01); *A61N 1/362* (2013.01); *A61N 1/36128* (2013.01)

(58) Field of Classification Search
CPC ...... A61N 1/37252; A61N 1/08; A61N 1/362; A61N 1/025; A61N 1/36128; A61N 1/0563
See application file for complete search history.

(56) References Cited

U.S. PATENT DOCUMENTS

| | | | | | |
|---|---|---|---|---|---|
| 6,161,043 | A | * | 12/2000 | McClure | A61B 5/0006 607/27 |
| 10,842,442 | B2 | * | 11/2020 | Lim | A61B 5/316 |
| 2003/0045908 | A1 | * | 3/2003 | Condie | A61B 5/366 607/9 |
| 2011/0054558 | A1 | * | 3/2011 | Gunderson | A61N 1/3702 607/27 |

(Continued)

OTHER PUBLICATIONS

Shamsollahi, Mohammad Bagher. "ECG denoising and compression using a modified extended Kalman filter structure." IEEE Transactions on Biomedical Engineering 55.9 (2008): 2240-2248. (Year: 2008).*

(Continued)

*Primary Examiner* — Gary Jackson
*Assistant Examiner* — Alexander M Eisenberg
(74) *Attorney, Agent, or Firm* — The Small Patent Law Group LLC; Dean D. Small

(57) ABSTRACT

An implantable medical device (IMD) and method are provided. The IMD includes a sensing channel configured to obtain biological signals indicative of biological behavior of an anatomy of interest over a period of time. The biological behavior has a feature of interest that repeats over time. The biological signals have clinically relevant (CR) segments that include information related to the feature of interest. The biological signals have non-clinically relevant (NCR) segments that do not include information related to the feature of interest. At least one of circuitry or a processor are configured to compare the biological signals to an amplitude window to distinguish the CR segments from the NCR segments, save to memory the CR segments and delete the NCR segments, save to memory time information indicative of a duration of the NCR segments that were deleted and to form a lossy compressed data set for the biological signals.

23 Claims, 6 Drawing Sheets

(56) References Cited

U.S. PATENT DOCUMENTS

| | | | |
|---|---|---|---|
| 2011/0196247 A1* | 8/2011 | Cao | A61B 5/7203 600/509 |
| 2012/0203123 A1* | 8/2012 | Mahajan | A61B 5/024 600/509 |
| 2016/0000350 A1* | 1/2016 | Zhang | A61B 5/7221 600/512 |
| 2016/0150989 A1* | 6/2016 | Felix | A61B 5/0006 600/523 |
| 2018/0174414 A1* | 6/2018 | Edpalm | H04N 19/124 |

OTHER PUBLICATIONS

Qian, Jia, et al. "A noble double-dictionary-based ECG compression technique for IoTH." IEEE Internet of Things Journal 7.10 (2020): 10160-10170. (Year: 2020).*

Lukin, Vladimir, et al. "Lossy compression of multichannel ECG based on 2-D DCT and pre-processing." 2008 International Conference on "Modern Problems of Radio Engineering, Telecommunications and Computer Science" (TCSET). IEEE, 2008. (Year: 2008).*

S. K. Mukhopadhyay, S. Mitra & M. Mitra (2015) A combined application of lossless and lossy compression in ECG processing and transmission via GSM-based SMS, Journal of Medical Engineering & Technology, 39:2, 105-122, DOI: 10.3109/03091902. 2014.990159 (Year: 2015).*

Viknesh, V., and P. Ram Prashanth. "Matlab implementation of ECG signal processing." IOSR Journal of VLSI and Signal Processing 3.1 (2013). (Year: 2013).*

Nemati, Kamyar, and Kannan Ramakrishnan. "Hybrid lossless and lossy compression technique for ECG signals." 2017 Third International Conference on Sensing, Signal Processing and Security (ICSSS). IEEE, 2017. (Year: 2017).*

* cited by examiner

METHOD AND DEVICE FOR MANAGING BIOLOGICAL ACTIVITY DATA STORAGE UTILIZING LOSSY COMPRESSION

BACKGROUND

Embodiments of the present disclosure generally relate to methods and devices for managing biological activity data storage using lossy compression.

Implantable medical devices are commonly used to acquire and store biological data signals, such as cardiac signals and neurological signals. For example, the biological data signals may include an intra-cardiac electrocardiogram (IEGM). At least some known implantable medical devices use a time-based sampling system, in which all biological data is sampled at a fixed time step. This fixed time step generally corresponds to a sample rate of an analog-to-digital converter (ADC) used by the implantable medical device.

The acquired signal is generally processed to extract features of interest (e.g., amplitude information, morphology features, QRS intervals). Further, the acquired signal is also sent to a memory device for storage. If an event of interest is detected, the data stored before and after the event of interest can be retrieved and analyzed.

Notably, for at least some known implantable medical devices, the majority of time spent processing and storing data is of limited clinical relevance, as clinical events of interest happen relatively infrequently. A trade-off exists between the amount of memory available due to size and power constraints and the desired amount of biological data signals to store in the IMD. Known compression techniques (e.g., ZIP file format and the like) may be employed to manage the amount of unneeded or clinically insignificant data stored on an IMD. Such compression techniques may be software-based and/or involve lossless compression techniques. Lossless compression techniques may require static data and relatively large amounts of computational resources, rendering them impractical or undesirable for implementation on an IMD to process biological data signals (e.g., IEGM signals). Accordingly, a need remains for methods and devices that more efficiently process and store biological data signals based on the content of the biological data signals that overcomes the foregoing and other disadvantages of conventional lossless and/or software based compression approaches.

SUMMARY

In accordance with embodiments herein, an implantable medical device (IMD) is provided. The IMD includes a sensing channel configured to obtain biological signals indicative of biological behavior of an anatomy of interest over a period of time. The biological behavior has a feature of interest that repeats over time. The biological signals have clinically relevant (CR) segments that include information related to the feature of interest. The biological signals have non-clinically relevant (NCR) segments that do not include information related to the feature of interest. The IMD includes memory to store specific executable instructions. At least one of circuitry or one or more processors are configured to execute the specific executable instructions to compare the biological signals to an amplitude window to distinguish the CR segments from the NCR segments, save to memory the CR segments and delete the NCR segments, save to memory time information indicative of a duration of the NCR segments that were deleted between the CR segments stored and automatically iteratively repeat the obtain, compare and save to form a lossy compressed data set for the biological signals.

Optionally, the lossy compressed data may include a non-lossy digital data set from the biological signals within the CR segments and a gap or null data set for the NCR segments. A circular buffer may be configured to store the biological signals. The at least one of circuitry or one or more processors may be configured to compare the biological signals in the circular buffer to the amplitude window and transfer the CR segments from the circular buffer to the memory and delete the NCR segments from the circular buffer. The time information may include at least one of the following for at least one of the NCR segments: i) a count of a number of samples from the biological signal in the at least one of the NCR segments; ii) time stamps for a beginning and an end of the at least one of the NCR segments; or iii) time stamps for a beginning and an end of successive CR segments before and after the at least one of the NCR segments.

Optionally, the biological signals may correspond to cardiac activity (CA) signals indicative of a series of beats and the feature of interest includes one or more of the P-wave, R-wave or T-wave from the series of beats. The lossy compressed data set may include digitized data defining a waveform shape of the PQRST waveform. The NCR segment may correspond to noise in the biological signals between the feature of interest that repeats over time. The amplitude window may include upper and lower boundaries. The one or more processors may be configured to identify portions of the biological signals that fall between the upper and lower boundaries as the NCR segments and to identify portions of the biological signals that are above the upper boundary and below the lower boundary as the CR segments.

Optionally, the IMD is one of an implantable cardiac monitor, a subcutaneous implantable cardioverter defibrillator, a cardiac rhythm management device, a pacemaker, a defibrillator, a neurostimulation device, or a pulmonary arterial pressure measurement device. The sensing channel may be configured to obtain one or more of cardiac activity signals, neurological activity signals, pressure signals, microfluidics test device signals or temperature signatures.

In accordance with embodiments herein, a method for managing cardiac activity data storage is provided. The method is under control of one or more processors configured with specific executable instructions. The method obtains biological signals indicative of biological behavior of an anatomy of interest over a period of time. The biological behavior has a feature of interest that repeats over time. The biological signals has clinically relevant (CR) segments that include information related to the feature of interest. The biological signals have non-clinically relevant (NCR) segments that do not include information related to the feature of interest. The method compares the biological signals to an amplitude window to distinguish the CR segments from the NCR segments. The method saves to memory the CR segments and delete the NCR segments and saves to memory time information indicative of a duration of the NCR segments that were deleted between the CR segments stored. The method automatically iteratively repeat the obtain, compare and save to form a lossy compressed data set for the biological signals.

Optionally, the lossy compressed data may include a non-lossy digital data set from the biological signals within the CR segments and a gap or null data set for the NCR segments. The one or more processors may be further configured to compare the biological signals in a circular buffer to the amplitude window, the circular buffer configured to store the biological signals and transfer the CR segments from the circular buffer to the memory and delete the NCR segments from the circular buffer. The time information may include at least one of the following for at least one of the NCR segments: i) a count of a number of samples from the biological signal in the at least one of the NCR segments; ii) time stamps for a beginning and an end of the at least one of the NCR segments; or iii) time stamps for a beginning and an end of successive CR segments before and after the at least one of the NCR segments.

Optionally, the biological signals may correspond to cardiac activity (CA) signals indicative of a series of beats and the feature of interest includes one or more of the P-wave, R-wave or T-wave from the series of beats. The lossy compressed data set may include digitized data defining a waveform shape of the PQRST waveform. The NCR segment may correspond to noise in the biological signals between the feature of interest that repeats over time. The amplitude window may include upper and lower boundaries.

Optionally, the one or more processors may be further configured to identify portions of the biological signals that fall between the upper and lower boundaries as the NCR segments and to identify portions of the biological signals that are above the upper boundary and below the lower boundary as the CR segments. The IMD may be one of an implantable cardiac monitor, a subcutaneous implantable cardioverter defibrillator, a cardiac rhythm management device, a pacemaker, a defibrillator, a neurostimulation device, or a pulmonary arterial pressure measurement device. The sensing channel may be configured to obtain one or more of cardiac activity signals, neurological activity signals, pressure signals, microfluidics test device signals or temperature signatures.

DETAILED DESCRIPTION

Figure 1:
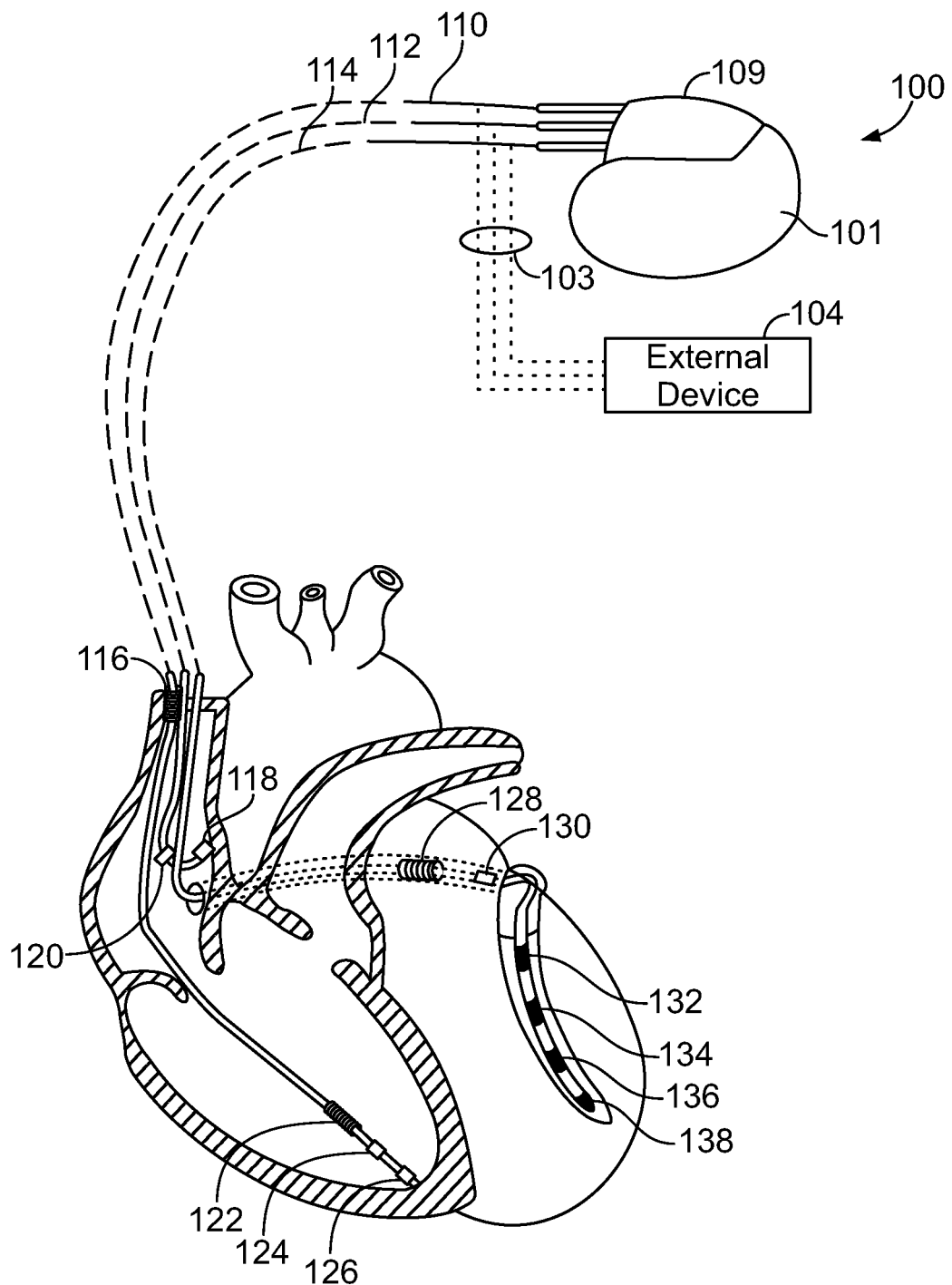
FIG. 1 illustrates an IMD and external device coupled to a heart in a patient and implemented in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The term "lossy compression" shall mean a type of data encoding that uses partial data discarding by 1) deleting select segments of the data and 2) saving other select segments of the data in either 2i) the original form or 2ii) as an inexact approximation of the select segments of data.

The terms "biological signal" and "biological data signal" shall mean a signal that is indicative of biological behavior of an anatomy of interest over a period of time, the biological behavior having a feature of interest that repeats over time. Biological signals may include clinically relevant (CR) segments that include information related to the feature of interest and non-clinically relevant (NCR) segments that do not include information related to the feature of interest. The NCR segments may correspond to noise in the biological signals between the feature of interest that repeats over time. Examples of biological signals include one or more of cardiac activity signals, neurological activity signals, pressure signals, BGA signals, temperature signatures, or the like. In some examples, the biological signals may represent electrical activity of interest that can be analyzed to discern biological signals that are pathognomonic of one or more particular diseases or conditions of interest. Biological data signals may include one or more of intra-cardiac electrocardiogram (IEGM) signals, CA signals, accelerometer signatures, deep brain signals, pressure signals, temperature signals, and the like. For example, the biological signals may correspond to CA signals indicative of a series of beats and the feature of interest may include one or more of the P-wave, R-wave, or T-wave from the series of beats.

The term "null data set" shall mean a data set corresponding to one or more non-clinically relevant segments of a biological signal that do not include information related to the feature of interest aside from time information associated with the one or more NCR segments. For example, the null data set may include fixed data values based on pre-programmed values and/or the last value at a converter before entering a window defined by one or more NCR segments. For example, a null data set may be a relatively short data set, such as one or two words or packets of data only indicating the fixed value and the start and stop time of the NCR data. Examples of the time information associated with a null data set may include at least one of the following for at least one of the NCR segments: i) a count of a number of samples from the biological signal in the at least one of the NCR segments; ii) time stamps for a beginning and an end of the at least one of the NCR segments; or iii) time stamps for a beginning and an end of successive CR segments before and after the at least one of the NCR segments.

The term "obtain" or "obtaining", as used in connection with data, signals, information and the like, includes at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

System Overview

Embodiments herein provide for systems, devices, and methods for managing biological data storage using lossy compression. An implantable medical device includes a sensing channel that acquires a biological data signal. The IMD may include, as part of IMD hardware, custom and/or semi-integrated circuits for implementing at least a portion of the methods for managing biological data. The IMD includes an amplitude window comparator communicatively coupled to the sensing channel that compares the values of the biological data signal to distinguish the CR data segments from the NCR data segments. Data that is only changing within a select amplitude window (e.g., a small amplitude window) having little clinical relevance is deemed to be NCR data. In contrast, data changing outside of the select amplitude window is deemed to be CR data. The IMD stores biological data that is changing beyond the select amplitude window (or CR data segments) for future analysis but does not store biological data that only changes within the select amplitude window (or NCR data segments). The IMD also stores time information associated with the beginning and end of the one or more NCR data segments. A processing and storage component communicatively coupled to the filtering component stores the CR data segments and the time information associated with the NCR data segments.

Embodiments may be implemented in connection with one or more implantable medical devices (IMDs). Non-limiting examples of IMDs include one or more of microfluidics devices, neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference in their entireties.

Additionally or alternatively, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference in their entireties. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference in their entireties.

Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

Additionally or alternatively, the IMD may be a leadless cardiac monitor (ICM) that includes one or more structural and/or functional aspects of the device(s) described in U.S. patent application Ser. No. 15/084,373, filed Mar. 29, 2016, entitled, "Method And System To Discriminate Rhythm Patterns In Cardiac Activity," which is hereby incorporated by reference in its entirety. Additionally or alternatively, the IMD may be an ICM that includes one or more structural and/or functional aspects of the device(s) and/or method(s) described in U.S. patent application Ser. No. 15/973,126, titled "Method And System For Second Pass Confirmation Of Detected Cardiac Arrhythmic Patterns"; U.S. patent application Ser. No. 15/973,351, titled "Method And System To Detect R-Waves In Cardiac Arrhythmic Patterns"; U.S. patent application Ser. No. 15/973,307, titled "Method And System To Detect Post Ventricular Contractions In Cardiac Arrhythmic Patterns"; and U.S. patent application Ser. No. 16/399,813, titled "Method And System To Detect Noise In Cardiac Arrhythmic Patterns".

Embodiments may be implemented in connection with one or more passive implantable medical devices (PIMDs). Non-limiting examples of PIMDs may include passive wireless sensors used by themselves, or incorporated into or used in conjunction with other implantable medical devices (IMDs) such as cardiac monitoring devices, pacemakers, cardioverters, cardiac rhythm management devices, defibrillators, neurostimulators, leadless monitoring devices, leadless pacemakers, replacement valves, shunts, grafts, drug elution devices, blood glucose monitoring systems, orthopedic implants, and the like. For example, the PIMD may include one or more structural and/or functional aspects of the device(s) described in U.S. Pat. No. 9,265,428 entitled "Implantable Wireless Sensor", U.S. Pat. No. 8,278,941 entitled "Strain Monitoring System and Apparatus", U.S. Pat. No. 8,026,729 entitled "System and Apparatus for In-Vivo Assessment of Relative Position of an Implant", U.S. Pat. No. 8,870,787 entitled "Ventricular Shunt System and Method", and U.S. Pat. No. 9,653,926 entitled "Physical Property Sensor with Active Electronic Circuit and Wireless Power and Data Transmission", which are all hereby incorporated by reference in their respective entireties.

Additionally or alternatively, the IMD may be a microfluidics test device that includes one or more structural and/or functional aspects of the methods, devices and systems described in the following publications, all of which are incorporated herein by reference in their entireties: U.S. Pat. No. 8,514,086, entitled "Displays For A Medical Device", issued Aug. 20, 2013; U.S. Patent Publication Number 2011/0256024, entitled "Modular Analyte Monitoring Device", published Oct. 20, 2011; U.S. Patent Publication Number 2010/0198142, entitled "Multifunction Analyte Test Device And Methods Therefore", published Aug. 5, 2010; U.S. Patent Publication Number 2011/0160544, entitled "System And Method For Analysis Of Medical Data To Encourage Healthcare Management", published Jun. 30, 2011; U.S. Pat. No. 5,294,404, entitled "Reagent Pack For Immunoassays" issued Mar. 15, 1994; U.S. Pat. No. 5,063,081, entitled "Method Of Manufacturing A Plurality Of Uniform Microfabricated Sensing Devices Having An Immobilized Ligand Receptor" issued Nov. 5, 1991; U.S. Pat. No. 7,419,821, entitled "Apparatus And Methods For Analyte Measurement And Immunoassay" issued Sep. 2, 2008; U.S. Patent Publication Number 2004/0018577, entitled "Multiple Hybrid Immunoassays" published Jan. 29, 2004; U.S. Pat. No. 7,682,833, entitled "Immunoassay Device With Improved Sample Closure" issued Mar. 23, 2010; U.S. Pat. No. 7,723,099, entitled "Immunoassay Device With Immuno-Reference Electrode" issued May 25, 2010; and Baj-Rossi et al. "Fabrication And Packaging Of A Fully Implantable Biosensor Array", (2013) IEEE, pages 166-169. The term "microfluidics test device" and shall mean any and all equipment, devices, and disposable products utilized to collect and analyze biological data that include microfluidics.

All references, including publications, patent applications and patents, cited herein are hereby incorporated by reference to the same extent as if each reference were individually and specifically indicated to be incorporated by reference and were set forth in its entirety herein.

FIG. 1 illustrates an IMD 100 and external device 104 coupled to a heart in a patient and implemented in accordance with embodiments herein. The external device 104 may be a programmer, an external defibrillator, a workstation, a portable computer, a personal digital assistant, a cell phone, a tablet computer, a bedside monitor, or the like. The IMD 100 may represent a cardiac monitoring device, pacemaker, cardioverter, cardiac rhythm management device, defibrillator, neurostimulator, leadless monitoring device, leadless pacemaker or the like, implemented in accordance with one embodiment of the present invention. The IMD 100 may be a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto. The IMD 100 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. Exemplary structures for the IMD 100 are discussed and illustrated in the drawings herewith.

The IMD 100 includes a housing 101 that is joined to a header assembly 109 that holds receptacle connectors connected to a right ventricular lead 110, a right atrial lead 112, and a coronary sinus lead 114, respectively. The leads 112, 114 and 110 measure cardiac signals of the heart. The right atrial lead 112 includes an atrial tip electrode 118 and an atrial ring electrode 120. The coronary sinus lead 114 includes a left atrial ring electrode 128, a left atrial coil electrode 130 and one or more left ventricular electrodes 132-138 (e.g., also referred to as P1, M1, M2 and D1) to form a multi-pole LV electrode combination. The right ventricular lead 110 includes an RV tip electrode 126, an RV ring electrode 124, an RV coil electrode 122, and an SVC coil electrode 116. The leads 112, 114 and 110 detect IEGM signals that are processed and analyzed as described herein. The leads 112, 114 and 110 also delivery therapies as described herein.

During implantation, the external device 104 is connected to one or more of the leads 112, 114 and 110 through temporary inputs 103. The inputs 103 of the external device 104 receive IEGM signals from the leads 112, 114 and 110 during implantation and display the IEGM signals to the physician on a display. Optionally, the external device 104 may not be directly connected to the leads 112, 114 and 110. Instead, the IEGM cardiac signals sensed by the leads 112, 114 and 110 may be collected by the IMD 100 and transmitted wirelessly to the external device 104. Hence, the external device 104 receives the IEGM cardiac signals through telemetry circuit inputs. The physician or another user controls operation of the external device 104 through a user interface.

Implantable Medical Device

Figure 2:
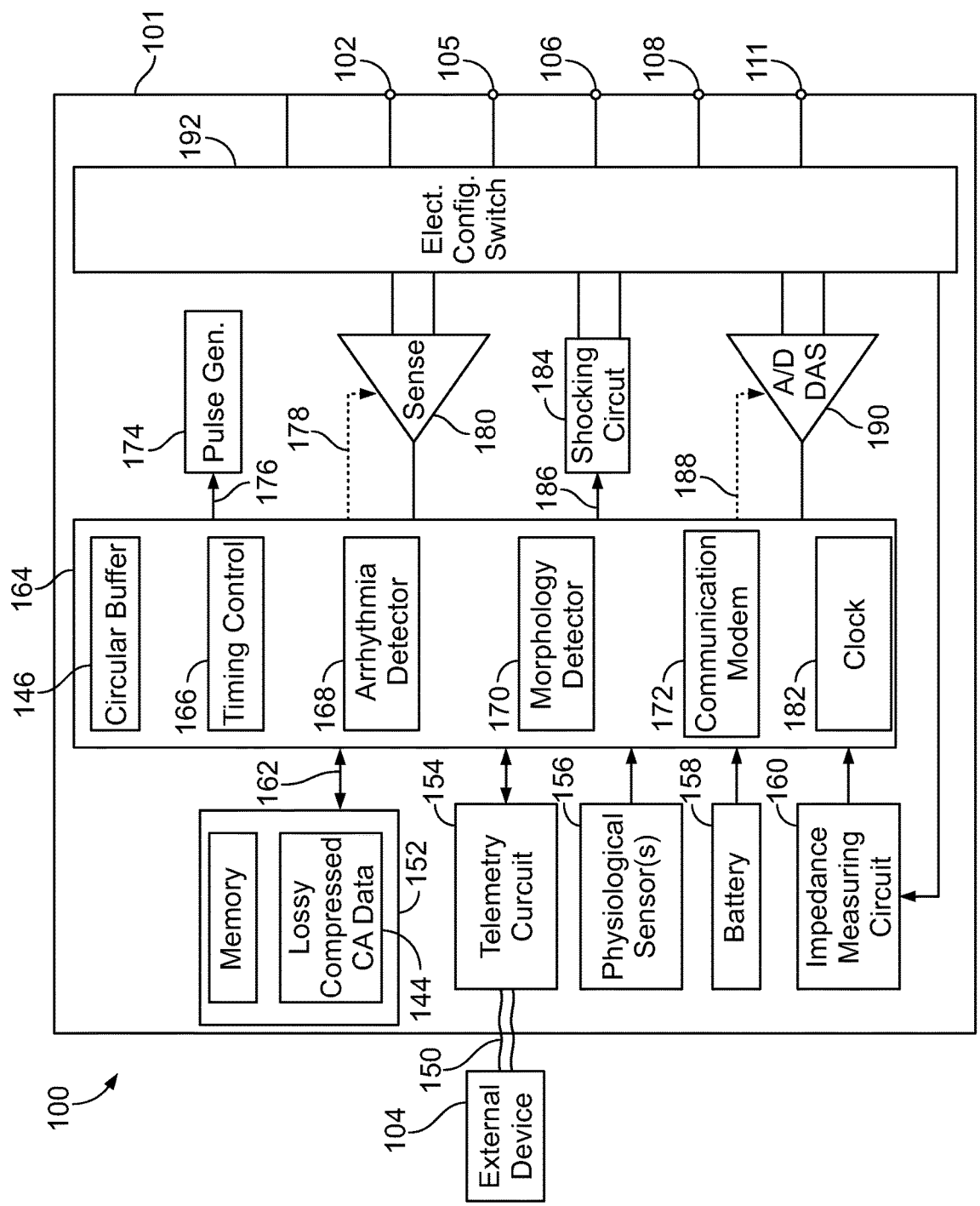
FIG. 2 illustrates a block diagram of the IMD of FIG. 1 in accordance with embodiments herein.

FIG. 2 illustrates a block diagram of the IMD 100 of FIG. 1 in accordance with embodiments herein. The IMD 100 may be implemented as a full-function biventricular pacemaker, equipped with both atrial and ventricular sensing and pacing circuitry for four chamber sensing and stimulation therapy (including both pacing and shock treatment). Optionally, the IMD 100 may provide full-function cardiac resynchronization therapy. Alternatively, the IMD 100 may be implemented with a reduced set of functions and components. For instance, the IMD may be implemented without ventricular sensing and pacing.

The IMD 100 has a housing 101 to hold the electronic/computing components. The housing 101 (which is often referred to as the "can", "case", "encasing", or "case electrode") may be programmably selected to act as the return electrode for certain stimulus modes. The housing 101 further includes a connector (not shown) with a plurality of terminals 102, 105, 106, 108, and 111. The terminals may be connected to electrodes that are located in various locations within and about the heart. For example, the terminals may include: a terminal 102 to be coupled to an first electrode (e.g., a tip electrode) located in a first chamber; a terminal 105 to be coupled to a second electrode (e.g., tip electrode) located in a second chamber; a terminal 106 to be coupled to an electrode (e.g., ring) located in the first chamber; a terminal 108 to be coupled to an electrode located (e.g., ring electrode) in the second chamber; and a terminal 111 to be coupled to an electrode (e.g., coil) located in the SVC. The type and location of each electrode may vary. For example, the electrodes may include various combinations of ring, tip, coil and shocking electrodes and the like.

The IMD 100 includes a programmable microcontroller 164 that controls various operations of the IMD 100, including cardiac monitoring and stimulation therapy. Microcontroller 164 includes one or more microprocessors or CPUs (or equivalent control circuitry), RAM and/or ROM memory, logic and timing circuitry, state machine circuitry, and I/O circuitry.

The IMD 100 further includes a first chamber pulse generator 174 that generates stimulation pulses for delivery by one or more electrodes coupled thereto. The pulse generator 174 may deliver pacing pulses and/or anti-tachy pacing therapy. The pulse generator 174 is controlled by the microcontroller 164 via control signal 176. The pulse generator 174 is coupled to the select electrode(s) via an electrode configuration switch 192, which includes multiple switches for connecting the desired electrodes to the appropriate I/O circuits, thereby facilitating electrode programmability. The switch 192 is controlled by a control signal 186 from the microcontroller 164. In the example of FIG. 2, a single pulse generator 174 is illustrated. Optionally, the IMD 100 may include multiple pulse generators, similar to pulse generator 174, where each pulse generator is coupled to one or more electrodes and controlled by the microcontroller 164 to deliver select stimulus pulse(s) to the corresponding one or more electrodes.

The microcontroller 164 is illustrated to include timing control circuitry 166 to control the timing of the stimulation pulses (e.g., pacing rate, atrio-ventricular (AV) delay, atrial interconduction (A-A) delay, or ventricular interconduction (V-V) delay, etc.). The timing control circuitry 166 may also be used for the timing of refractory periods, blanking intervals, noise detection windows, evoked response windows, alert intervals, marker channel timing, and so on. Microcontroller 164 also has an arrhythmia detector 168 for detecting arrhythmia conditions, and a morphology detector 170 to review and analyze one or more features of the morphology of cardiac signals. Although not shown, the microcontroller 164 may further include other dedicated circuitry and/or firmware/software components that assist in monitoring various conditions of the patient's heart and managing pacing therapies.

The microcontroller 164 includes a clock 182 to, among other things, manage lossy compression. The clock 182 may be characterized by a frequency. The frequency of the clock may be related to a sampling rate at which the IMD 100 acquires biological signals.

A circular buffer 146 is provided that is configured to store the biological signals. The biological signals may be recorded in a circular buffer. A circular buffer is an allocated section of memory in which the newest data is continuously stored in the section of memory that stores the oldest data. The buffer may be large enough to retain biological signals for a desired duration and/or sampled values (e.g., 30-60 seconds and/or 15-30 sampled values). For example, the buffer may be provided with a size sufficient to retain 10,000 sampled values of a biological signal. Based on a sampling frequency of 1000 Hz, retaining 10,000 sampled values retains a 10 s segment of the biological signal. The circular buffer 146 may either be implemented within the microcontroller 164, within the memory 152, or in other firmware or circuitry that is coupled to the microcontroller 164.

The IMD 100 is equipped with a communication modem (modulator/demodulator) 172 to enable wireless communication with other devices, implanted devices and/or external devices. In one implementation, the communication modem 172 may use high frequency modulation of a signal transmitted between a pair of electrodes. In one implementation, the communication modem 172 uses high frequency modulation, for example using RF, Bluetooth, or Bluetooth Low Energy telemetry protocols. The signals are transmitted in a high frequency range and will travel through the body tissue in fluids without stimulating the heart or being felt by the patient. The communication modem 172 may be implemented in hardware as part of the microcontroller 164, or as software/firmware instructions programmed into and executed by the microcontroller 164. Alternatively, the communication modem 172 may reside separately from the microcontroller as a standalone component. The communication modem 172 facilitates data retrieval from a remote monitoring network. The communication modem 172 enables timely and accurate data transfer directly from the patient to an electronic device utilized by a physician.

The IMD 100 includes sensing circuitry 180 selectively coupled to one or more electrodes that is configured to obtain biological signals indicative of biological behavior of an anatomy of interest over a period of time. The sensing circuitry 180 performs sensing operations through the switch 192 to detect the presence of cardiac activity in the right chambers of the heart. The sensing circuitry 180 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The output of the sensing circuitry 180 is connected to the microcontroller 164 which, in turn, triggers or inhibits the pulse generator 174 in response to the absence or presence of cardiac activity. The sensing circuitry 180 receives a control signal 178 from the microcontroller 164 for purposes of controlling the gain, threshold, polarization charge removal circuitry (not shown), and the timing of any blocking circuitry (not shown) coupled to the inputs of the sensing circuitry.

In the example of FIG. 2, a single sensing circuit 180 is illustrated. Optionally, the IMD 100 may include multiple sensing circuits, similar to sensing circuit 180, where each sensing circuit is coupled to one or more electrodes and controlled by the microcontroller 164 to sense electrical activity detected at the corresponding one or more electrodes. The sensing circuit 180 may operate in a unipolar sensing configuration or in a bipolar sensing configuration.

The IMD 100 further includes an analog-to-digital (A/D) data acquisition system (DAS) 190 coupled to one or more electrodes via the switch 192 to sample cardiac signals across any pair of desired electrodes. The data acquisition system 190 is configured to acquire intracardiac electrogram signals, convert the raw analog data into digital data, and store the digital data for later processing and/or telemetric transmission to an external device 104 (e.g., a programmer, local transceiver, or a diagnostic system analyzer). The data acquisition system 190 is controlled by a control signal 188 from the microcontroller 164.

The microcontroller 164 is coupled to a memory 152 by a suitable data/address bus 162. The programmable operating parameters used by the microcontroller 164 are stored in memory 152 and used to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy. The lossy compressed CA data set 144 may also be stored in memory for future analysis. The memory 152 is configured to store, as the lossy compressed CA data set 144, a data set in which select segments of the CA data have been deleted and other select segments of the CA data saved in either i) the original form or ii) as an inexact approximation of the saved select segments of CA data.

The operating parameters of the IMD 100 may be non-invasively programmed into the memory 152 through a telemetry circuit 154 in telemetric communication via communication link 150 with the external device 104. The telemetry circuit 154 allows intracardiac electrograms and status information relating to the operation of the IMD 100 (as contained in the microcontroller 164 or memory 152) to be sent to the external device 104 through the established communication link 150.

The IMD 100 may further include magnet detection circuitry (not shown), coupled to the microcontroller 164, to detect when a magnet is placed over the unit. A magnet may be used by a clinician to perform various test functions of the unit 100 and/or to signal the microcontroller 164 that the external programmer is in place to receive or transmit data to the microcontroller 164 through the telemetry circuits 154.

The IMD 100 may further include one or more physiologic sensors 156. Such sensors are commonly referred to as "rate-responsive" sensors because they are typically used to adjust pacing stimulation rates according to the exercise state of the patient. However, the physiological sensor 156 may further be used to detect changes in cardiac output, changes in the physiological condition of the heart, or diurnal changes in activity (e.g., detecting sleep and wake states). Signals generated by the physiological sensors 156 are passed to the microcontroller 164 for analysis. The microcontroller 164 responds by adjusting the various pacing parameters (such as rate, AV Delay, V-V Delay, etc.) at which the atrial and ventricular pacing pulses are administered. While shown as being included within the unit 100, the physiologic sensor(s) 156 may be external to the unit 100, yet still be implanted within or carried by the patient.

Examples of physiologic sensors might include sensors that, for example, sense respiration rate, pH of blood, ventricular gradient, activity, position/posture, minute ventilation (MV), and so forth.

A battery 158 provides operating power to all of the components in the IMD 100. The battery 158 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 158 also desirably has a predictable discharge characteristic so that elective replacement time can be detected. As one example, the unit 100 employs lithium/silver vanadium oxide batteries.

Optionally, the IMD 100 further includes an impedance measuring circuit 160, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 160 is coupled to the switch 192 so that any desired electrode may be used. Optionally, the microcontroller 164 further controls a shocking circuit 184 by way of a control signal 186. The shocking circuit 184 generates shocking pulses of low (e.g., up to 0.5 joules), moderate (e.g., 0.5-10 joules), or high energy (e.g., 111 to 40 joules), as controlled by the microcontroller 164.

The IMD 100 may be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 164 further controls a shocking circuit 184 by way of a control signal 186. The shocking circuit 180 generates shocking pulses of low (e.g., up to 0.5 joules), moderate (e.g., 0.5-10 joules), or high energy (e.g., 11 to 40 joules), as controlled by the microcontroller 164. Such shocking pulses are applied to the patient's heart through shocking electrodes. It is noted that the shock therapy circuitry is optional and may not be implemented in the IMD, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the IMD 100.

It is recognized that the configurations of circuitry and microcontrollers illustrated herein are by way of example only. Optionally, operations described in connection with the microcontroller may be implemented by circuitry (e.g., firmware and/or discrete circuitry). Optionally, operations described in connection with the circuitry (e.g., firmware and/or discrete circuitry) may be implemented by the microcontroller.

Figure 3A:
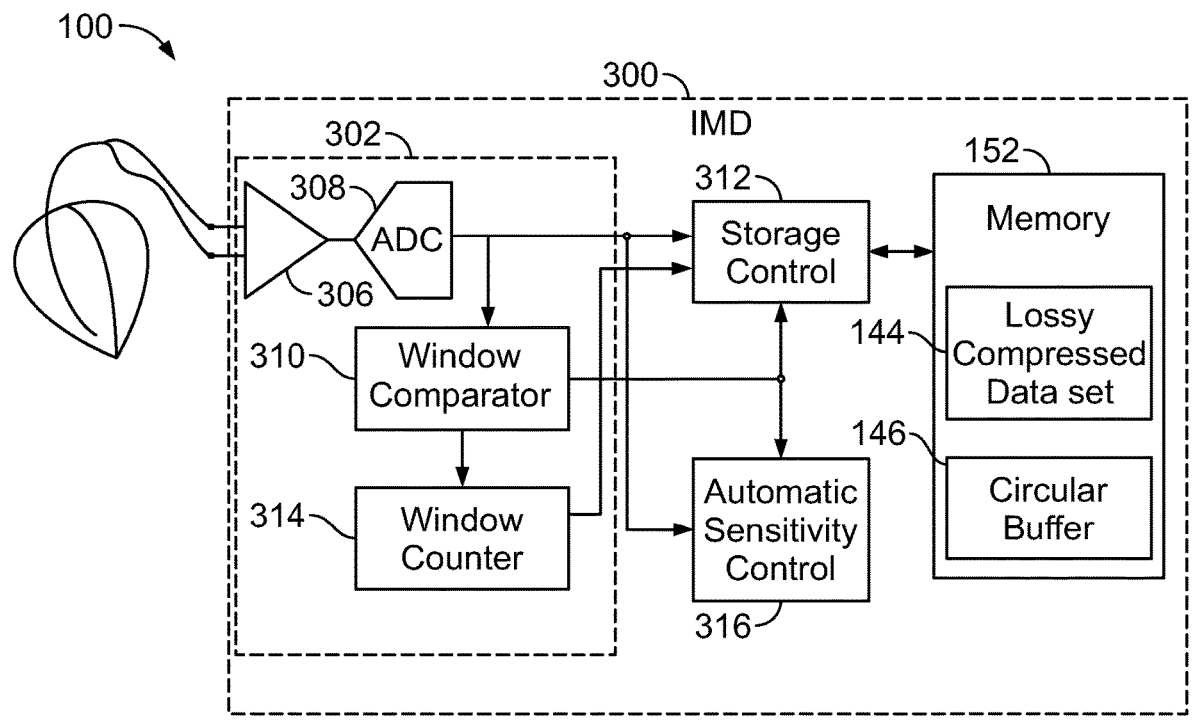
FIG. 3A illustrates a block diagram of one example of a sensing channel of the IMD of FIG. 2 in accordance with embodiments herein.

FIG. 3A illustrates a block diagram of one example of a sensing channel of the IMD of FIG. 2 in accordance with embodiments herein. The sensing channel 300 includes various circuitry that may be configured to obtain biological signals, such as one or more of CA signals, neurological activity signals, pressure signals, microfluidics test device signals, temperature signatures, or the like. The IMD 100 may be electrically coupled to a biological system of interest (e.g., the heart, a target neural tissue, etc.). The sensing channel 300 may be configured to obtain biological signals indicative of biological behavior of an anatomy of interest over a period of time. The biological behavior may have a feature of interest that repeats over time (e.g., an R-wave, P-wave, T-wave, or the like). A sensing front end 302 may include, among other things, the sensing circuitry 180 and/or the DAS 190 of FIG. 2. The sensing front end 302 may acquire biological signals. A sensing amplifier 306 may amplify the biological signals and an A/D converter 308 may digitize the biological signals. Digitized biological signals output by the A/D converter 308 may be passed to one or more of an amplitude window comparator 310, a storage control unit 312, and/or an automatic sensitivity control (ASC) unit 316 for further processing to compile a lossy compressed data set as described further below.

In accordance with one or more embodiments, the amplitude window comparator 310 may compare the biological signals to an amplitude window to distinguish the CR segments from the NCR segments. The amplitude window comparator 310 may determine whether or not the biological signals fall within the amplitude window. Optionally, the comparison may be implemented by one or more microcontrollers. The amplitude window includes upper and lower boundaries. The comparator is configured to identify portions of the biological signals that fall between the upper and lower boundaries as the NCR segments and to identify portions of the biological signals that are above the upper boundary and below the lower boundary as the CR segments. Segments of the biological signals that fall outside of the amplitude window may be deemed to be CR data segments that include information related to the feature of interest. The amplitude window comparator 310 outputs a signal (e.g., a non-zero set value) to the storage control unit 312 indicating that the CR data segments in the circular buffer 146 are to be stored in memory 152 as part of a lossy compressed data set (e.g., the lossy compressed CA data set 144) based on detecting CR data segments. Conversely, segments of the biological signals falling within the amplitude window may be deemed to be NCR data segments. NCR segments may correspond to noise in the biological signals between the periodic feature of interest and/or portions of the biological signals that do not contain clinically relevant data. The amplitude window comparator 310 outputs an alert and/or a signal (e.g., a set value of zero) to the storage control unit 312 indicating that the NCR data segments in the circular buffer 146 are to be ignored (e.g., discarded, not stored in memory 152) based on detecting NCR data segments. Additionally or alternatively, the storage control unit 312 may store gaps and/or null data sets corresponding to NCR data segments. The null data sets do not include information related to the feature of interest and may include one or more pre-programmed and/or fixed values. For example, a null data set may be a relatively short data set, such as one or two words or packets of data only indicating the fixed value and the start and stop time of the NCR data.

Additionally or alternatively, the amplitude window comparator 310 is configured to compare each data sample of the biological signals to the upper and lower boundaries of the amplitude window. When a data sample exceeds the upper limit of the amplitude window or falls below the lower limit of the amplitude window, the comparator provides an output (outside window alert) indicating that the data sample is either above the upper limit or below the lower limit of the amplitude window. The outside window alert is provided to a counter 314 and to the storage control unit 312. In response to receiving the outside window alert, the counter 314 increments a count tracking the number of data samples that are outside of the amplitude window. The counter 314 provides the count value to the storage control unit 312. The counter 312 may provide the count value to the storage control unit 312 each time the count is incremented and/or only when the count exceeds a threshold (e.g., 10, 15, etc.). Based on the outside window alert and the count, the storage control unit 312 manages storage of the sampled values of the biological signal in the circular buffer 146 as described further below.

Additionally or alternatively, the counter 314 may transmit the count value corresponding to an NCR data segment to the storage control unit 312 to be stored as part of the lossy compressed data set (e.g., as a marker) once a new CR data set is detected. The count value and the sample rate (e.g., 100 Hz) of the sensing channel 300 indicate the duration of the NCR segments of the lossy compressed CA data set 144.

Additionally or alternatively, the sensing channel 300 may use the count value of the counter 314 to determine whether a current biological signal forms part of an NCR data segment that falls within the amplitude window or forms part of a CR data segment that is merely passing through the amplitude window. For example, when a number of data samples falling within the window amplitude exceeds a threshold count value, the amplitude window comparator 310 may provide an output to the storage control unit 312 indicating the end of a CR data segment at a select data sample and/or a number of select data samples to ignore in the circular buffer 146. Conversely, when a number of data samples falling within the window amplitude falls below the threshold count value, the data samples are deemed to correspond to a CR data segment passing through the amplitude window and the amplitude window comparator 310 continues to output an outside window alert. Additionally or alternatively, the counter 314 may be reset based on determining that the current biological signal corresponds to a CR data segment that falls outside of the amplitude window (e.g., based on reaching a select number of samples falling outside of the amplitude window).

Based on the amplitude window comparator 310 detecting CR or NCR data segments, the biological signals may be stored in memory 152 as part of a lossy compressed data set (e.g., the lossy compressed CA data set 144) for subsequent analysis and review or ignored, respectively. The storage control unit 312 may also receive and store the count of the number of samples (or a count value) corresponding to the NCR data segments in memory 152 as part of and/or in conjunction with the lossy compressed data set. The count value corresponding to the NCR data segments may be used to reconstruct the duration of the NCR segments of the lossy compressed data set for subsequent display and/or analysis.

The ASC 316 may be configured to determine the features of interest of the biological signals (e.g., R-R intervals, etc.). For example, the ASC 316 may store a threshold that, once crossed, marks a new feature of interest (e.g., a new R-wave). The ASC 316 may receive the digitized biological signals from the A/D converter 308 and the signals generated by the amplitude window comparator 310. The signals generated by the amplitude window comparator 310 may indicate to the ASC 316 when to start and stop storing the CR data segments.

Figure 3B:
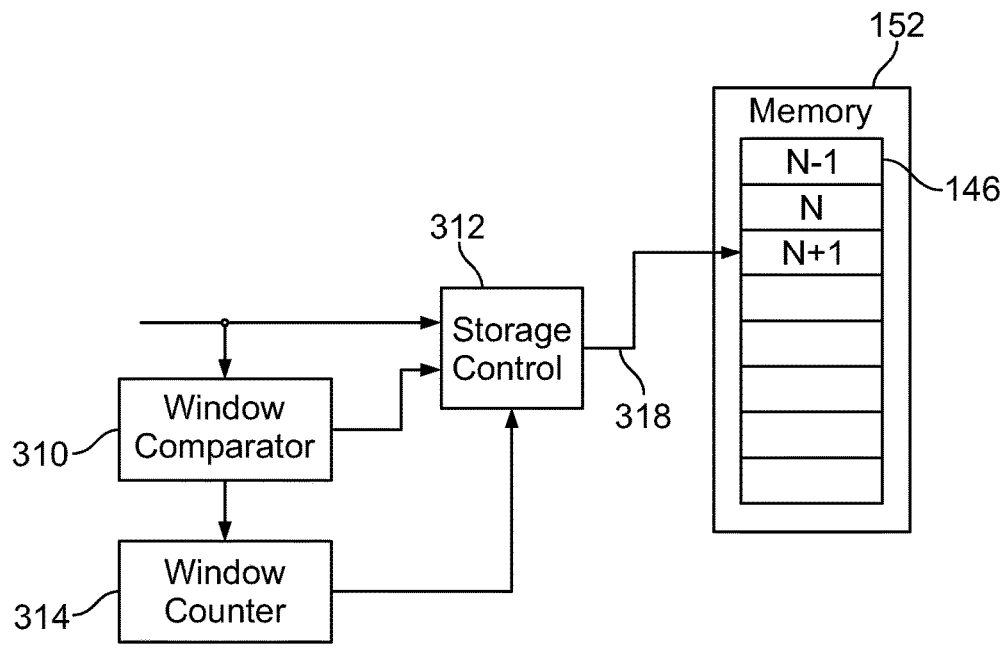
FIG. 3B illustrates one example of the storage control unit and memory of FIG. 3A in accordance with embodiments herein.

FIG. 3B illustrates one example of the storage control unit 312 and memory 152 of FIG. 3A in accordance with embodiments herein. The storage control unit 312 may receive the digitized biological signals from the A/D converter 308 and store sampled values of the biological signals in the circular buffer 146. The circular buffer 146 may be a loop recorder that continuously stores segments of the biological signals (e.g., the waveform). N−1, N, and N+1 represent the addresses of sampled values of a biological signal stored in the circular buffer 146. The storage control unit 312 may manage the circular buffer 146 based on the output of the amplitude window comparator 310 and/or the counter 314 to store at least a portion of the lossy compressed CA data set 144. For example, the storage control unit 312 may update an address pointer 318 to the address of the most recent sampled value as new data is stored in the circular buffer 146. The storage control unit 312 may update the address pointer 318 based on the amplitude window comparator 310 outputting an outside window alert (e.g., a non-zero set value). The storage control unit 312 may move the address pointer 318 back by the count value of the counter 314 based on the amplitude window comparator 310 outputting a signal indicating that the sampled values correspond to an NCR data segment. For example, based on the amplitude window comparator 310 outputting a signal indicating that two sampled values (stored at N and N+1) of the biological signals fall within the amplitude window and correspond to an NCR data segment (e.g. a set value of zero), the storage control unit 312 moves the address pointer 318 back two places in the circular buffer 146 to the last sampled value of the last CR segment (stored at N−1), thereby ignoring and/or not storing the two samples values corresponding to the NCR data segment in the lossy compressed CA data set 144. The storage control unit 312 may continue to move the address pointer 318 back to the address of the sampled value of the last CR segment (e.g., N−1), erasing sampled values stored at N, based on the amplitude window comparator 310 outputting the within window signal. The storage control unit 312 may resume updating the address pointer 318 based on the amplitude window comparator 310 outputting an outside window alert corresponding to the current sampled value stored at N.

Figure 4:
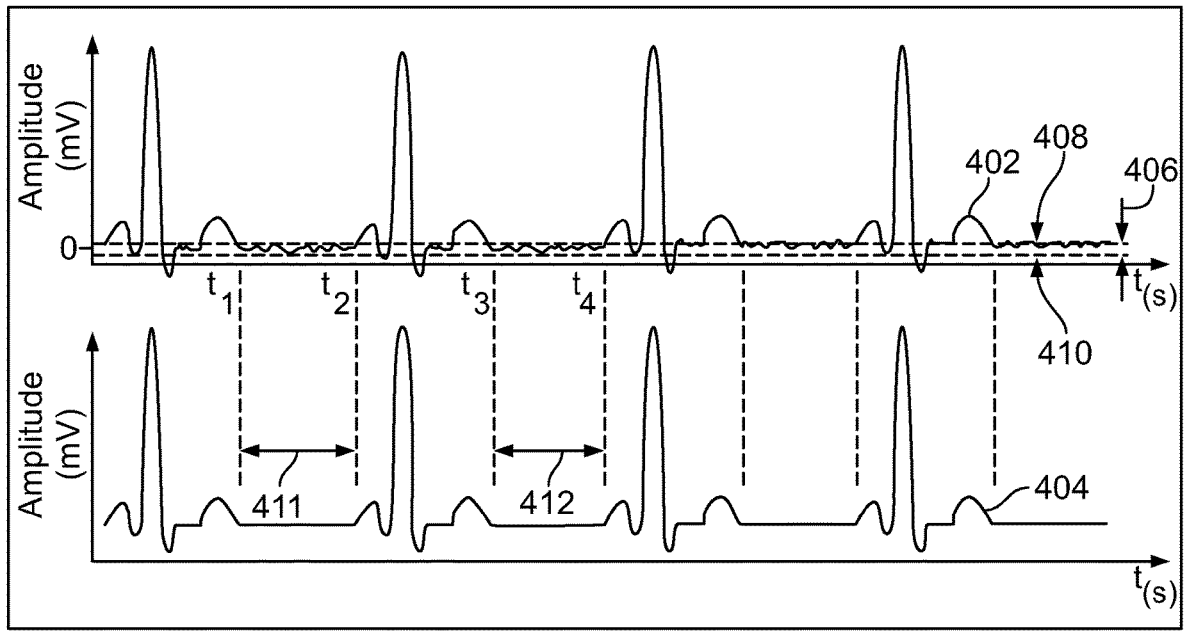
FIG. 4 is a plot of both an example biological signal and an example lossy compressed signal in accordance with embodiments herein.

FIG. 4 is a plot of both an example biological signal and an example lossy compressed signal in accordance with embodiments herein. The biological data signal 402 may be acquired by the sensing channel 300 of the IMD 100. The lossy compressed signal 404 may be generated by discriminating between the CR and NCR data segments of the biological data signal 402 using, among other things, the amplitude window comparator 310 of the IMD 100. In one example, the biological data signal may be an electrocardiogram (ECG). Additionally or alternatively, the biological data signal may be any signal capable of being processed using the systems and methods described herein.

A window (e.g., amplitude window 406) may be overlaid on biological data signal 402. The amplitude window 406 may be defined by an upper threshold 408 and a lower threshold 410. Values of the biological data signal 402 that fall within the amplitude window 406 and correspond to NCR data segments (i.e., values greater than or equal to lower threshold 410 and less than or equal to upper threshold 408) may be ignored and/or not stored in the lossy compressed signal 404. Specifically, values that fall within the amplitude window 406 and correspond to NCR data segments may be discarded and/or not subjected to the additional processing and/or storage that values falling outside of the amplitude window 406 and correspond to CR data segments undergo.

The amplitude window 406 may have a fixed size and position (i.e., upper and lower thresholds 408 and 410 may remain constant over time and amplitude window 406 may be centered on a baseline of the biological data signal 402).

Additionally or alternatively, the size and/or position of the amplitude window 406 may vary dynamically over time. For example, for some biological data signals, the baseline value may change over time and/or the size and/or position of the amplitude window 406 may vary over time as appropriate.

Although the values falling within amplitude window 406 may be ignored and/or discarded, the relative timing of events in the biological data signals (e.g., the duration of the NCR segments) may need to be preserved. Accordingly, the counter 314 (e.g., implemented using clock 182 of microcontroller 164) may track the total number of counts (e.g., the total number of samples obtained at the select frequency) during which the biological data signal falls within the amplitude window 306 and corresponds to an NCR data segment. The counts may be used to determine the duration of the NCR data segments. The counts corresponding to an NCR data segment may be processed and/or stored (e.g., as markers) to facilitate analyzing and/or displaying the biological data signal. For example, a first time interval 411 and a second time interval 412, each corresponding to NCR data segments, may be determined based on the number of counts associated with the respective NCR data segments.

In one embodiment, the amplitude window comparator 310 may be engaged and the output (i.e., the lossy compressed signal 404) may be set to a fixed value while the signal remains within amplitude window 406. The fixed value may be, for example, a pre-programmed value, or the last acquired value before the signal entered the amplitude window 406. As long the signal remains within amplitude window 406, no NCR data segments are stored in the lossy compressed data set 144. As described above, once the signal exits amplitude window 406, the ASC 316 may be enabled and resume determining features of interest in the CR data segments.

Figure 5:
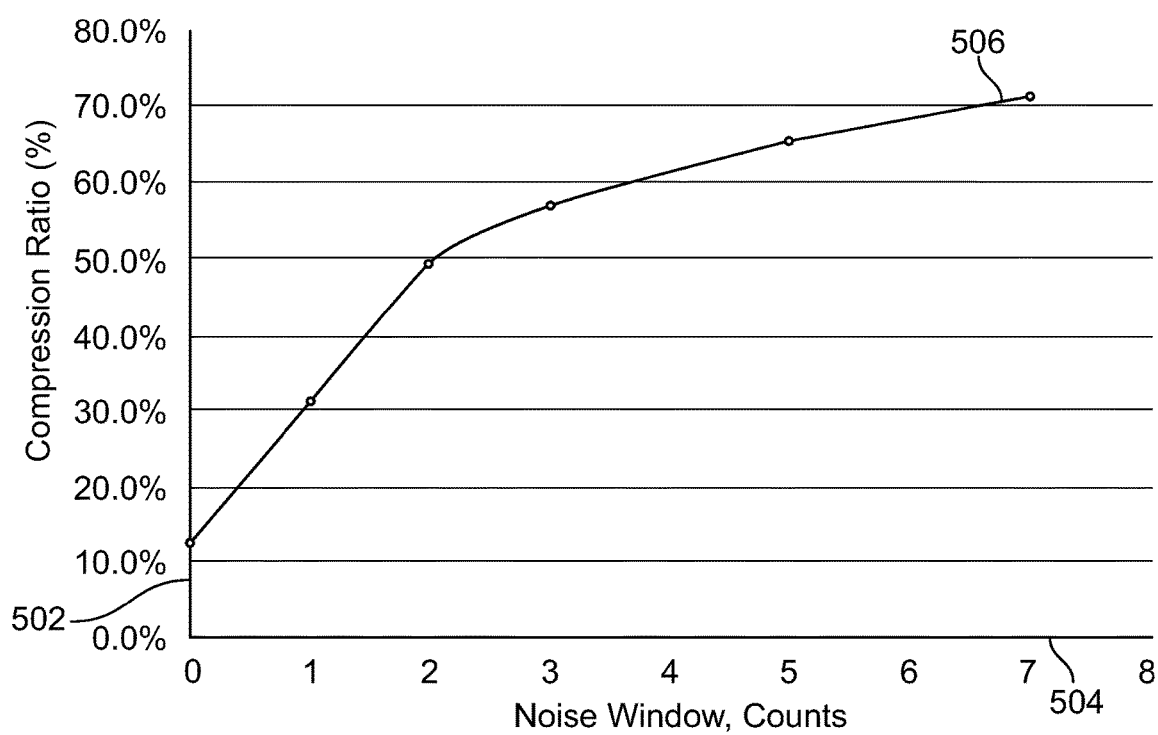
FIG. 5 illustrates an example plot of compression vs. amplitude window amplitude in accordance with one or more embodiments herein.

FIG. 5 illustrates an example of a plot of compression vs. amplitude window amplitude in accordance with one or more embodiments herein. Compression is represented on the axis 502 as a compression ratio. The compression ratio may be the size of the lossy CA data set 144 expressed as a percentage of the uncompressed CA data. The amplitude window amplitude is represented on the axis 504 as a count value (e.g., the number of samples falling within the amplitude window). The count value of the amplitude window (e.g., amplitude window 406) used by the amplitude window comparator 310 to distinguish the CR segments from the NCR segments of the biological data may be selected based on a level of compression and signal fidelity around a baseline. Trend line 506 illustrates that, as the count value of the amplitude window increases, the level of compression (e.g., the compression ratio) increases. Increased amounts of memory remain available for storage based on higher levels of compression of the lossy CA data set 144. For example, an amplitude window of 1 count corresponds to a compression ratio of approximately 30%, while an amplitude window of 7 counts corresponds to a maximum compression ratio of approximately 70%.

Figure 6:
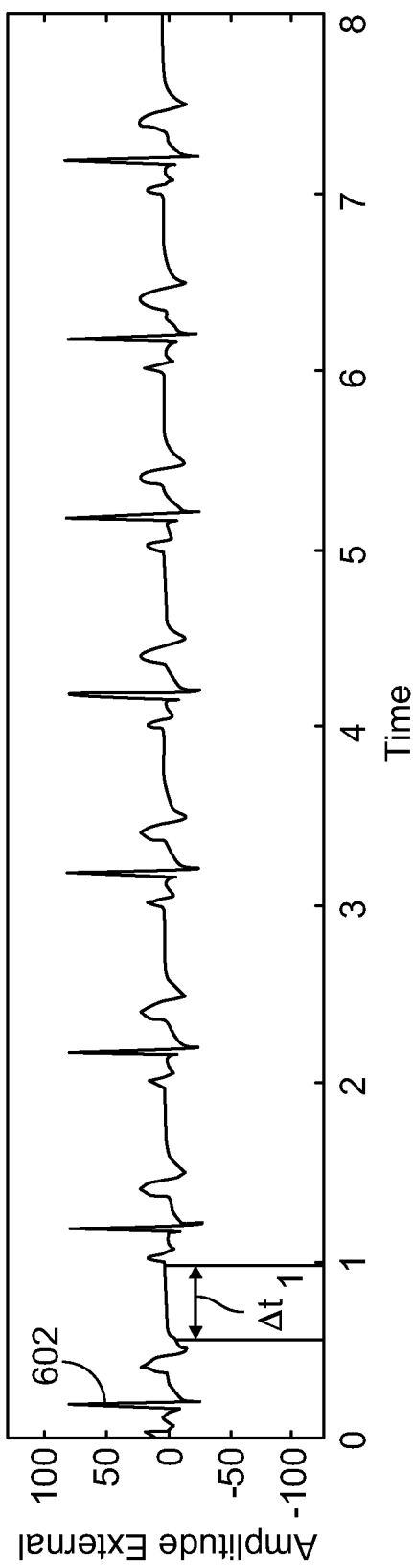
FIG. 6 is an example of a plot of an uncompressed biological data signal in accordance with embodiments herein.
Figure 7:
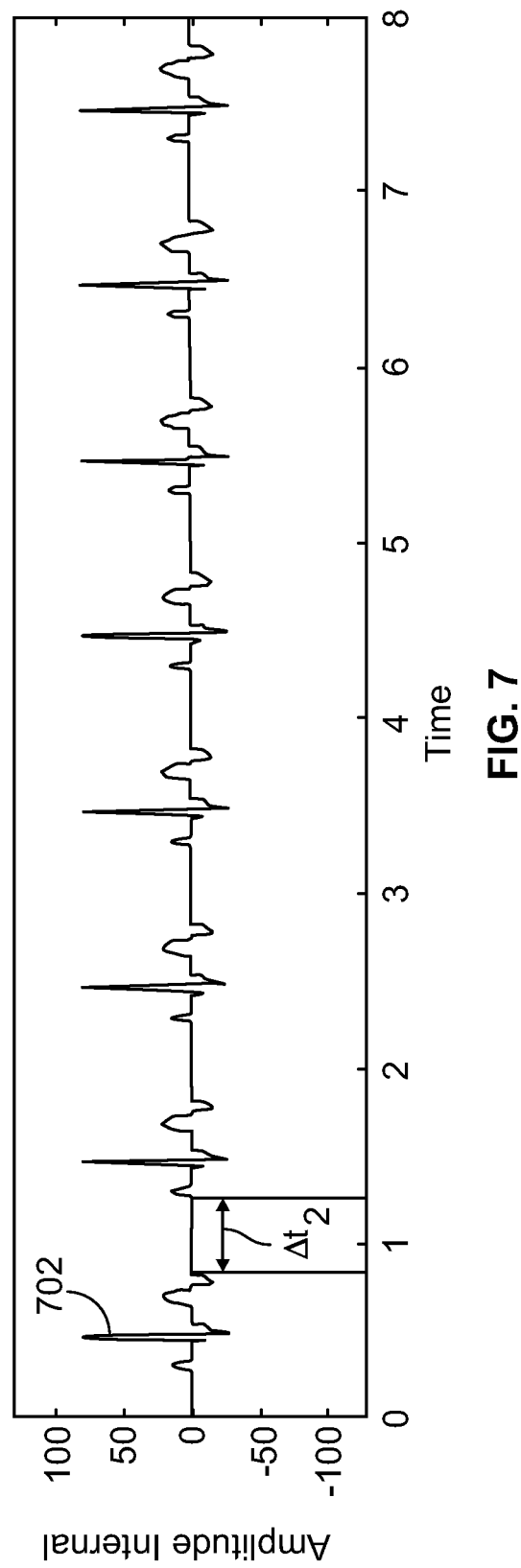
FIG. 7 is an example of a plot of a lossy compressed biological data signal in accordance with embodiments herein.

FIG. 6 is an example of a plot of an uncompressed biological data signal and FIG. 7 is an example of a plot of a lossy compressed biological data signal in accordance with embodiments herein. Trend line 602 in FIG. 6 represents an uncompressed 60 beat per minute ECG. Trend line 702 in FIG. 7 represents a lossy compressed 60 beat per minute ECG at maximum compression (e.g., a 70% compression ratio) based on the same ECG signal used for trend line 602. For example, for the same time period ($\Delta t_1$) corresponding to an NCR data segment, the uncompressed ECG signal data (trend line 602) shows all variation, regardless of clinical significance. In contrast, the lossy compressed ECG signal data (trend line 702) effectively ignores the portions of the ECG signal data that fall within the amplitude window and correspond to an NCR data segment, representing the NCR data segment with a fixed value for the duration of the NCR data segment. For a given type of biological data signal, the compression ratio may be managed based on the level of signal fidelity around the baseline (e.g., the X-axis). For example, the compression ratio may be selected to be a value less than the compression ratio that would render a given biological data signal too lossy for clinical reference.

Methods for Managing CA Data Storage

Figure 8:
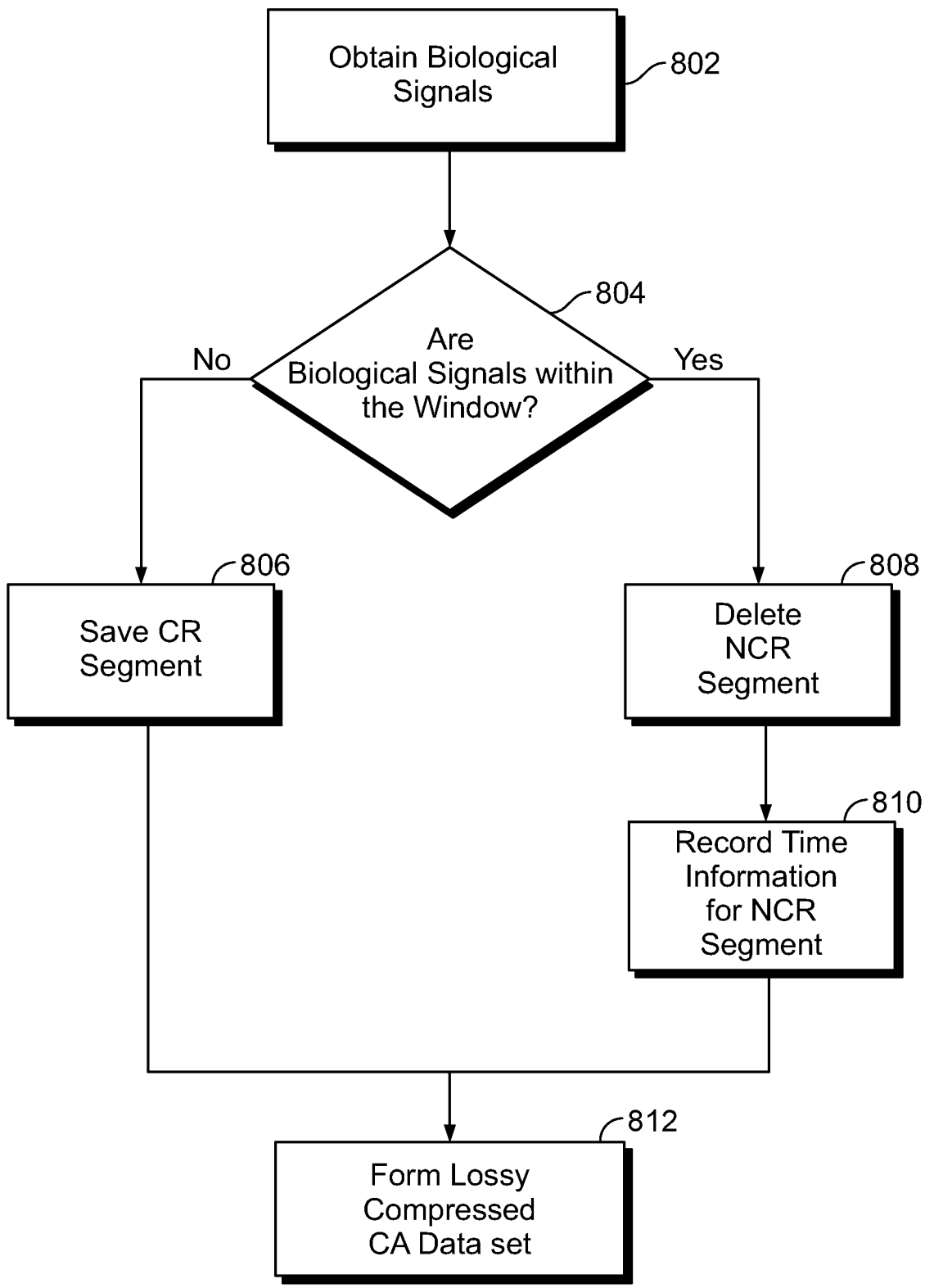
FIG. 8 illustrates a process for managing cardiac activity data storage carried out in accordance with embodiments herein.

FIG. 8 illustrates a process for managing cardiac activity data storage carried out in accordance with embodiments herein, such as in accordance with one or more of FIGS. 2-5. All or a portion of the operations of FIG. 8 may be implemented by one or more processors of the ICM 100 configured with executable instructions. Portions of the operations of FIG. 8 may also be implemented by one or more processors of one or more of a local external device and/or a remote server. Although the operations of FIG. 8 are described in at least a partially serial manner, it is recognized that at least a portion of the operations are performed in parallel. Furthermore, the operations of FIG. 8 may be performed in parallel with other operations of the IMD 100, such as operations related to other data streams obtained by the IMD 100.

At 802, one or more processors of the IMD 100 obtain biological signals indicative of biological behavior of an anatomy of interest over a period of time. The biological behavior includes a feature of interest that repeats over time. The biological signals include CR segments that include information related to the feature of interest and NCR segments that do not include information related to the feature of interest (e.g., corresponding to signal portions between the periodic feature of interest). The IMD 100 may obtain the biological signals over a sensing channel 300 at a sampling frequency (e.g., 100 Hz). The sensing channel 300 may be configured to obtain one or more of CA signals, neurological activity signals, pressure signals, microfluidics test device signals, temperature signatures, or the like. In an example, the biological signals may correspond to CA signals indicative of a series of beats and the feature of interest may include one or more of the P-wave, R-wave or T-wave from the series of beats (e.g., R-R intervals, etc.). For example, a sensing front end 302 may acquire biological signals, a sensing amplifier 306 may amplify the biological signals, and an A/D converter 308 may digitize the biological signals. The one or more processors of the IMD 100 may, among other things, temporarily store the biological signals in a circular buffer 146. Upon obtaining the biological signals, flow moves to 804.

At 804, one or more processors of the IMD 100 compare the biological signals to an amplitude window to distinguish the CR segments from the NCR segments. For example, the one or more processors of the IMD 100 may compare the biological signals in the circular buffer 146 to the amplitude window. The amplitude window (e.g., amplitude window 406) includes upper and lower boundaries and/or thresholds. The upper and lower boundaries of the amplitude window may remain constant over time. Additionally or alternatively, the amplitude window may be centered on a baseline (e.g., an amplitude value of zero) of the biological data signal. Further additionally or alternatively, the size and/or position of the amplitude window may vary dynamically over time. For example, for some biological data signals, the baseline value may change over time and the size and/or position of amplitude window may be varied over time as appropriate. The process identifies portions of the biological signals that fall between the upper and lower boundaries as the NCR segments and identifies portions of the biological signals that are above the upper boundary and below the lower boundary as the CR segments. Based on the process identifying CR segments, flow moves to 806. Conversely, based on identifying NCR segments, flow moves to 808.

At 806 and 808, one or more processors of the IMD 100 transfer the CR segments from the circular buffer to the memory and delete the NCR segments from the circular buffer. At 806, one or more processors of the IMD 100 save to memory the CR segments. For example, the process saves a non-lossy digital data set that includes the biological signals within the CR segments. The process may store the CR data segments and/or output an outside window signal (e.g., a non-zero set value) to the storage control unit 312 indicating that the CR data segments in the circular buffer 146 are to be stored in memory 152 as part of the lossy compressed CA data set 144 based on detecting CR data segments. Alternatively, at 808, one or more processors of the IMD 100 delete, ignore, or overwrite the NCR segments from the circular buffer and/or output an inside window signal (e.g., a set value of zero) to the storage control unit 312 indicating the NCR data segment in the circular buffer 146 are to be ignored. Additionally or alternatively, the process saves a gap or null data set corresponding the NCR segment in the lossy compressed data set.

At 810, one or more processors of the IMD 100 save to memory time information indicative of a duration of the NCR segments that were deleted between the CR segments stored. The time information may include at least one of the following for at least one of the NCR segments: i) a count of a number of samples from the biological signal in the at least one of the NCR segments; ii) time stamps for a beginning and an end of the at least one of the NCR segments; iii) time stamps for a beginning and an end of successive CR segments before and after the at least one of the NCR segments; or the like. A count of the number of samples from the biological signal of the NCR segments may be maintained by the counter 314 operatively coupled to the amplitude window comparator 310. The count corresponding to a given NCR data segment may be transmitted to the storage control unit 314 to be stored, e.g., as part of the lossy compressed data set. For example, the count may be stored as a marker. The count and the known data sampling rate may be used to reconstruct the duration of the NCR data segment for subsequent display and/or analysis.

At 812, one or more processors of the IMD 100 automatically iteratively repeat the obtain, compare and save to form a lossy compressed data set for the biological signals. The lossy compressed data may include the non-lossy digital data set from the biological signals within the CR segments and the gap or null data set for the NCR segments. The lossy compressed data set may also include the time information indicative of a duration of the NCR segments that were deleted between the stored CR segments. In one non-limiting example, the lossy compressed data set may include digitized data defining a waveform shape of a PQRST waveform for a CA signal.

Accordingly, the present systems, devices, and methods enable management of biological data storage using lossy compression for implementation on an IMD to process biological signals more efficiently and only store biological data signals based on the content of the biological data signals. Such systems, devices, and methods provide for discrimination between CR data segments and NCR data segments, conserving memory by disregarding data that is not clinically significant but preserving clinically significant data for display and/or analysis.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

All references, including publications, patent applications and patents, cited herein are hereby incorporated by reference to the same extent as if each reference were individually and specifically indicated to be incorporated by reference and were set forth in its entirety herein.

What is claimed is:

1. An implantable medical device (IMD), comprising:
   sensing circuitry configured to obtain biological signals indicative of biological behavior of an anatomy of interest over a period of time, wherein the sensing circuitry is configured to obtain, as the biological signals, one or more of cardiac activity signals, neurological activity signals, pressure signals, microfluidics test device signals or temperature signatures, the biological behavior having a feature of interest that repeats over time, the biological signals having clinically relevant (CR) segments that include information related to the feature of interest, the biological signals having non-clinically relevant (NCR) segments that do not include information related to the feature of interest;
   memory to store specific executable instructions;
   at least one of circuitry or one or more processors configured to execute the specific executable instructions to:
      compare the biological signals to an amplitude window to identify portions of the biological signals that fall outside the amplitude window to be the CR segments and to identify portions of the biological signals that fall within the amplitude window to be the NCR segments;
      save, to the memory, the CR segments as a non-lossy digital data set and delete the NCR segments between the CR segments, wherein a decision to save the CR segments to the memory and delete the NCR segments is based on the comparison of the biological signals to the amplitude window;
      save, to the memory, time information indicative of durations of the corresponding NCR segments that were deleted between the CR segments stored; and
      automatically iteratively repeat the compare and save to form a lossy compressed data set for the biological signals.

2. The IMD of claim 1, wherein the lossy compressed data includes the non-lossy digital data set from the biological signals within the CR segments in an original form and a gap or null data set for the NCR segments.

3. The IMD of claim 1, further comprising a circular buffer configured to store the biological signals, the at least one of circuitry or one or more processors configured to:
   compare the biological signals in the circular buffer to the amplitude window; and
   transfer the CR segments from the circular buffer to the memory and delete the NCR segments from the circular buffer.

4. The IMD of claim 1, wherein the time information includes at least one of the following for at least one of the NCR segments:
   i) a count of a number of samples from the biological signal in the at least one of the NCR segments;
   ii) time stamps for a beginning and an end of the at least one of the NCR segments; or
   iii) time stamps for a beginning and an end of successive CR segments before and after the at least one of the NCR segments.

5. The IMD of claim 1, wherein the biological signals correspond to cardiac activity (CA) signals indicative of a series of beats and the feature of interest includes one or more of a P-wave, R-wave or T-wave from the series of beats.

6. The IMD of claim 5, wherein the lossy compressed data set include digitized data defining a waveform shape of at least a portion of a PQRST waveform in an original form within the CR segments.

7. The IMD of claim 1, wherein the NCR segment corresponds to noise in the biological signals between the feature of interest that repeats over time.

8. The IMD of claim 1, wherein the amplitude window includes upper and lower boundaries, the one or more processors configured to identify portions of the biological signals that fall between the upper and lower boundaries as the NCR segments and to identify portions of the biological signals that are above the upper boundary and below the lower boundary as the CR segments, wherein a decision to save the CR segments to the memory and delete the NCR segments is based on the comparison of the biological signals to the amplitude window.

9. The IMD of claim 1, wherein the IMD is one of an implantable cardiac monitor, a subcutaneous implantable cardioverter defibrillator, a cardiac rhythm management device, a pacemaker, a defibrillator, a neurostimulation device, or a pulmonary arterial pressure measurement device.

10. The IMD of claim 1, wherein the lossy compressed data set transforms the biological signals by deleting NCR segments of the biological signals and saving CR segments of the biological signals in an original form.

11. The IMD of claim 1, wherein the non-lossy digital data set, saved to the memory of the IMD, retains an original form of the CR segment of the biological signal.

12. A method for managing cardiac activity data storage, comprising:
    under control of one or more processors, in an implantable medical device (IMD), configured with specific executable instructions:
    obtain biological signals indicative of biological behavior of an anatomy of interest over a period of time, the biological behavior having a feature of interest that repeats over time, the biological signals having clinically relevant (CR) segments that include information related to the feature of interest, the biological signals having non-clinically relevant (NCR) segments that do not include information related to the feature of interest;
    compare the biological signals to an amplitude window to identify portions of the biological signals that fall outside the amplitude window to be the CR segments and to identify portions of the biological signals that fall within the amplitude window to be the NCR segments;

save to memory, in the IMD, the CR segments as a non-lossy digital data set and delete the NCR segments between the CR segments wherein a decision to save the CR segments to the memory and delete the NCR segments is based on the comparison of the biological signals to the amplitude window;

save to the memory time information indicative of durations of the corresponding NCR segments that were deleted between the CR segments stored; and automatically iteratively repeat the compare and save to form a lossy compressed data set for the biological signals.

13. The method of claim 12, wherein the lossy compressed data includes the non-lossy digital data set of the biological signals within the CR segments in an original form and a gap or null data set for the NCR segments.

14. The method of claim 12, wherein the one or more processors are further configured to:

compare the biological signals in a circular buffer to the amplitude window, the circular buffer configured to store the biological signals; and transfer the CR segments from the circular buffer to the memory and delete the NCR segments from the circular buffer.

15. The method of claim 12, wherein the time information includes at least one of the following for at least one of the NCR segments:

i) a count of a number of samples from the biological signal in the at least one of the NCR segments;

ii) time stamps for a beginning and an end of the at least one of the NCR segments; or iii) time stamps for a beginning and an end of successive CR segments before and after the at least one of the NCR segments.

16. The method of claim 12, wherein the biological signals correspond to cardiac activity (CA) signals indicative of a series of beats and the feature of interest includes one or more of a P-wave, R-wave or T-wave from the series of beats.

17. The method of claim 16, wherein the lossy compressed data set include digitized data defining a waveform shape of at least a portion of a PQRST waveform in an original form within the CR segments.

18. The method of claim 12, wherein the NCR segment corresponds to noise in the biological signals between the feature of interest that repeats over time.

19. The method of claim 12, wherein the amplitude window includes upper and lower boundaries, wherein the one or more processors are further configured to identify portions of the biological signals that fall between the upper and lower boundaries as the NCR segments and to identify portions of the biological signals that are above the upper boundary and below the lower boundary as the CR segments, wherein a decision to save the CR segments to the memory and delete the NCR segments is based on the comparison of the biological signals to the amplitude window.

20. The method of claim 12, wherein the IMD is one of an implantable cardiac monitor, a subcutaneous implantable cardioverter defibrillator, a cardiac rhythm management device, a pacemaker, a defibrillator, a neurostimulation device, or a pulmonary arterial pressure measurement device.

21. The method of claim 12, wherein the IMD includes sensing circuitry that is configured to obtain one or more of cardiac activity signals, neurological activity signals, pressure signals, microfluidics test device signals or temperature signatures.

22. The method of claim 12, wherein the lossy compressed data set transforms the biological signals by deleting NCR segments of the biological signals and saving CR segments of the biological signals in an original form.

23. The method of claim 12, wherein the non-lossy digital data set, saved to the memory of the IMD, retains an original form of the CR segment of the biological signal.

* * * * *